| United States Patent [19] | [11] Patent Number: 4,535,167 |
| Freidinger | [45] Date of Patent: Aug. 13, 1985 |

[54] CHIRAL, N-PROTECTED, N-SUBSTITUTED α-AMINO ACIDS

[75] Inventor: Roger M. Freidinger, Hatfield, Pa.

[73] Assignee: Merck & Co. Inc., Rahway, N.J.

[21] Appl. No.: 497,301

[22] Filed: May 23, 1983

Related U.S. Application Data

[63] Continuation-in-part of Ser. No. 330,634, Dec. 14, 1981, abandoned.

[51] Int. Cl.$^3$ ............... C07C 125/065; C07C 103/46
[52] U.S. Cl. .................... 548/344; 548/477; 548/497; 260/465 D; 260/465.4; 260/464; 560/16; 560/24; 560/29; 560/32; 560/33; 560/45; 560/148; 560/158; 560/159; 560/160; 560/163; 560/165; 562/426; 562/439; 562/444; 562/450; 562/507; 562/557; 562/560; 562/561; 562/567; 562/571; 562/574
[58] Field of Search .............. 560/16, 29, 24, 32, 560/33, 115, 148, 158, 159, 163, 165, 160; 260/465 D, 465.4, 464; 548/344, 477, 497; 562/426, 439, 444, 450, 507, 557, 560, 561, 567, 571, 574

[56] References Cited

U.S. PATENT DOCUMENTS

| 2,413,856 | 1/1947 | Bersworth | 260/36 |
| 2,558,923 | 7/1951 | Bersworth | 260/534 |
| 2,564,092 | 8/1951 | Bersworth | 260/534 |
| 2,583,559 | 1/1952 | Frost | 260/534 |
| 3,872,099 | 3/1975 | Yasuda et al. | 260/326.4 |
| 3,933,783 | 1/1976 | Yasuda et al. | 260/112.5 |
| 3,984,417 | 10/1976 | Yasuda et al. | 260/287 |
| 4,108,846 | 8/1978 | Meienhofer | 260/112.5 |
| 4,199,499 | 4/1980 | Smithwick, Jr. et al. | 260/112.5 |

FOREIGN PATENT DOCUMENTS

| 514718 | 7/1955 | Canada . |
| 26-031706 | 3/1951 | Japan . |
| 597151 | 3/1978 | Switzerland . |

OTHER PUBLICATIONS

House, "Modern Synthetic Reactions", 2nd Ed., pp. 9 & 10, (1972).
Greenstein, "Chemistry of the Amino Acids," vol. 3, pp. 2761-2762, (1961).
Freidinger et al., J. Org. Chem. 48:77, (1983).
Ben-Ishai, J. Amer. Chem. Soc., 79:5736, (1957).
McDermott et al., Can. J. Chem., 51:1915, (1973).
Kursanov, Synthesis 633, (1974).
Auerbach, J. Org. Chem., 41:725, (1976).
Cheung et al., Can. J. Chem., 55:906, (1977).

*Primary Examiner*—Michael L. Shippen
*Attorney, Agent, or Firm*—Richard A. Elder; Hesna J. Pfeiffer; Julian S. Levitt

[57] ABSTRACT

Chiral N-protected, N-substituted α-amino acids are described. These compounds are prepared by condensation of an N-protected α-amino acid with an aldehyde followed by the selective reductive cleavage of an oxazolidinone intermediate.

4 Claims, No Drawings

CHIRAL, N-PROTECTED, N-SUBSTITUTED α-AMINO ACIDS

CROSS REFERENCE TO RELATED APPLICATION

This application is a continuation-in-part of copending application Ser. No. 330,634, filed Dec. 14, 1981 now abandoned.

BACKGROUND OF THE INVENTION

The present invention is directed to chiral, N-substituted α-amino acids. The present invention is also directed to an improved synthetic route to chiral N-substituted α-amino acids. The synthesis requires two steps, the first involving a condensation of a chiral, N-protected, α-amino acid with an aldehyde to form an oxazolidinone. The second step, reductive cleavage of the oxazolidinone C-O bond gives, without affecting either the N-protecting group, or the desired chirality, the N-protected, N-substituted α-amino acid.

A standard method of preparing N-protected, N-methyl amino acids is described in McDermott and Benoiton, *Canadian Journal of Chemistry*, 51, 1915 (1973) and Cheung and Benoiton, *Canadian Journal of Chemistry*, 55, 906 (1977). The procedure involves alkylation of an N-protected amino acid in the presence of sodium hydride. The process fails for certain amino acids and is limited to the formation of N-methyl amino acids.

Unprotected N-methyl amino acids have been prepared by the catalytic hydrogenation of an oxazolidinone intermediate formed by the reaction of an N-protected α-amino acid and paraformaldehyde. See for example, Pless in Swiss Patent No. 597,151 (Derwent No. 27069A). This method is limited to the production of N-methyl α-amino acids.

The synthetic method of the instant invention has several advantages over the prior art; (1) the reaction is more general, in that it is not limited to the formation of N-methyl amino acids, (2) the present invention utilizes acid-catalyzed conditions, and (3) the chirality of the starting material is preserved. Acidic conditions allow for the use of base sensitive protecting groups, thus giving versatility to the reaction sequence See for example, Meienhofer, U.S. Pat. No. 4,108,846. By the terms "preserving chirality", it is understood that the process of the present invention does not effect any change in the chiral center of the starting α-amino acid. That is, for example, L-amino acids will retain the "L" configuration when N-substituted under the present process.

SUMMARY OF THE INVENTION

This invention is directed toward chiral N-substituted α-amino acids and to a process for preparing these compounds. A chiral amino acid is reacted with an aldehyde to form an oxazolidinone intermediate and the selective reduction of this intermediate yields the chiral, N-protected, N-substituted α-amino acid. The use of base sensitive, acid stabile N-protecting groups such as Fmoc, allows for versatility in the synthetic route, and the use of mild, selective reducing agents, such as triethylsilane/trifluoracetic acid allow for the survival of the N-protecting group during the oxazolidinone reduction.

DETAILED DESCRIPTION OF THE INVENTION

By definition, the α-amino acids include those naturally occurring amino acids with the amine group on the carbon α to the carboxyl group such as; the so called "essential amino acids", alanine, valine, leucine glycine, isoleucine, phenylalanine, tyrosine, threonine, cysteine, cystine, methionine, aspartic acid, glutamic acid, arginine, lysine, ornithine, histidine, serine, tryptophan and the like. The term "N-protected or N-protecting group" as used herein after to the base sensitive, acid stabile protecting groups described below. The term "loweralkyl", as used herein, includes those straight or branched, saturated or unsaturated $C_1$-$C_{10}$ carbon fragments typified by methyl, ethyl, hexyl, octyl, decyl and the like.

The process of the present invention may be illustrated by the following reaction scheme:

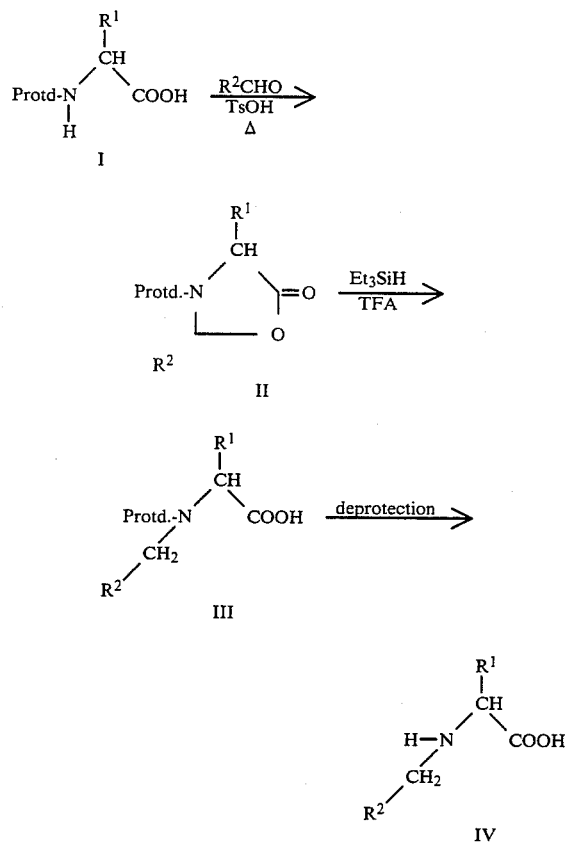

Protd. = base labile protecting group.

The initial step in the synthetic route of the instant invention is the condensation reaction of a chiral, N-protected α-amino acid (I) with a suitable aldehyde to form an oxazolidinone intermediate (II). As depicted above in Scheme I, the α-amino acid (I) may be typified by the following $R^1$ groups:

$CH_3-$, $(CH_3)_2CH-$, $(CH_3)_2CHCH_2-$, $HOCH_2-$,

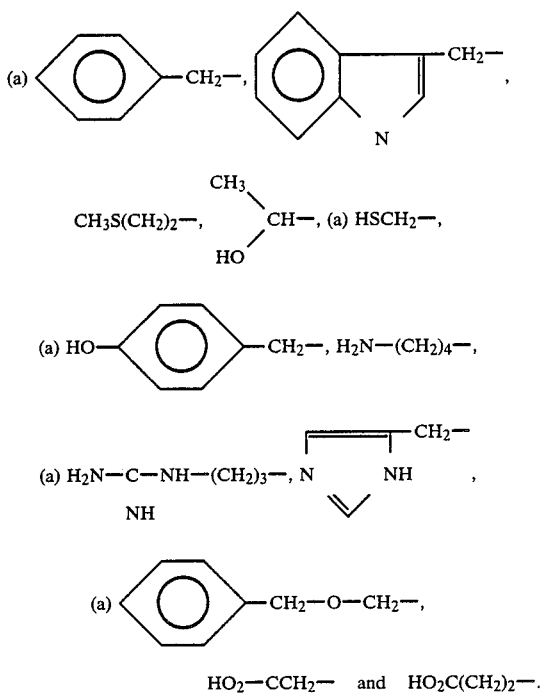

HO₂—CCH₂— and HO₂C(CH₂)₂—.

In more general terms, the $R^1$ group may be defined as: loweralkyl, hydroxyloweralkyl, mercaptoloweralkyl, aminoloweralkyl, mono- or di-loweralkylaminoloweralkyl, loweralkylthioloweralkyl, phenyl, benzyl, phenylloweralkyl, p-hyroxybenzyl, indolylloweralkyl, phthalimidylloweralkyl, imidazolylloweralkyl, benzyloxyloweralkyl, guanidinoloweralkyl, carboxyloweralkyl and loweralkylcarboxyloweralkyl. Note: Reactive functional groups on the $R^1$ groups listed above with (a) require the use of a conventional protecting group such as benzyl, phthalimidyl, 2,4-dinitrophenyl, and the like.

Suitable aldehydes ($R^2$CHO) include those straight or branched $C_1$-$C_{22}$ alkyl aldehydes exemplified by, but not limited to; ethanal, propanal, butanal, pentanal, hexanal, heptanal and the like. The aldehyde may be saturated or contain one or more sites of unsaturation, for example propenal, butenal, hexenal, heptenal and the like. In addition to the alkyl aldehydes described, cyclic ring containing aldehydes may also be employed. For example, benzaldehyde, cyclohexanecarboxaldehyde, phenylacetaldehyde, and the like will suffice in this process.

The process step in this synthetic sequence requires the selective reductive cleavage of the oxazolidinone C-O bond without the removal of the N-protecting group.

The selective reduction reaction may generally be accomplished by use of the "ionic hydrogenation" reaction described by Kursanov et al., in *Synthesis* 633 (1974). This reaction requires a proton donor, for example, a medium strenth acid such as trifluoroacetic acid, and a hydride ion donor. Typical useful hydride ion sources include the organosilanes. In addition to the organosilanes, dihydroaromatic hydrocarbons may serve as hydride ion donors. Use of such compounds allows for the use of stronger acids than trifluoroacetic acid for the proton source. Acids such as p-toluenesulfonic acid, sulfuric acid solutions, acetic acid solutions and the like may be employed. The preferred combination in the present application is a loweralkylorganosilane such as triethylsilane and trifluoroacetic acid.

The acidic conditions of the selective reduction reaction require the use of acid stabile N-protecting groups such as the 9-fluorenylmethoxycarbonyl (Fmoc), trifluoroacetyl (Tfa), 4-toluenesulfonylethyloxycarbonyl (Tsoc), carbobenzoxy (Cbz), and aromatic halogenated derivatives thereof (e.g., 2-chloro-Cbz) methylsulfonylethyloxycarbonyl (Mesoc), 2-(triphenylphosphino)-ethoxycarbonyl (Peoc), and 2-cyano-t-butyloxycarbonyl (Cyoc) which are assuming an increased importance in synthetic peptide chemistry. Of the N-protecting groups described above, the Fmoc group is the most preferred for use in the synthetic route of the instant invention.

Conventional synthetic procedures may be used both for protecting and deprotecting the α-amino acid nitrogen with the nitrogen protecting groups listed above. For example, formation of the Fmoc protected α-amino acid involves reaction of the α-amino acid in a mixture of dioxane and water with Fmoc-Cl and $Na_2CO_3$. Removal of the Fmoc protecting group to yield compounds of Formula IV may generally be accomplished by treating the protected compound with an organic base, for example, piperidine at room temperature for a time period of from 0.5 to 24 hours.

The standard reaction conditions for the formation of the oxazolidinone intermediate (II) involve reacting the N-protected α-amino acid with the aldehyde in a suitable inert solvent, with a temperature range of from room temperature (20° C.) to reflux temperature, for example, refluxing toluene with an acid catalyst such as a catalytic amount of para-toluenesulfonic acid for a time period of from 0.5 to 24 hours.

The preferred reaction conditions for achieving the selective reductive cleavage of the C-O bond of the oxazolidinone intermediate involve using triethylsilane and trifluoroacetic acid in a suitable solvent such as chloroform at room temperature for from 2 to 30 hours.

Chiral unprotected compounds of Formula (IV) generated via the process of the present invention are useful as pharmaceuticals, especially as anti-inflammatory agents.

For treatment of inflammation in humans a chiral unprotected compound of Formula (IV) would be administered in an effective amount in an appropriate dosage form, via an acceptable pharmaceutical carrier.

Any suitable route of administration would be used such as oral, parenteral, intramuscular and the like. The appropriate dosage forms are exemplified by tablets, troches, dispersions, suspensions, solutions, capsules and the like for oral administration; suspensions, solutions, emulsions and the like for parenteral administration.

A convenient daily dose in humans would be on the order of from 20 to 2000 mg, preferably from 40 to 1000 mg, most preferably from 100 to 500 mg of an unprotected, chiral, N-substituted α-amino acid of Formula IV. A convenient dosage regime would call for administration of one or more dosage units, for example from one to four times a day, not to exceed the daily dose total.

In addition to the pharmaceutically useful compounds available by the present process, N-substituted α-amino acids are known to have other utilities. For example, N-alkyl and N-alkenyl substituted α-amino acids and their alkali earth metal salts have been used as detergent additives as shown in Japanese Kokai Koho No. 51,031,706 (Derwent No. 32870X).

The chiral, N-protected, N-substituted α-amino acids of Formula III are also useful as intermediates in conventional peptide syntheses. See for example, Yasuda et al., U.S. Pat. Nos., 3,933,783; 3,872,099; and 3,984,417, each of which is directed to peptide synthesis employing N-protected amino acids as one of the reactants.

The following examples will more fully illustrate the practice of this invention. It will be readily understood by the skilled artisan that these examples are not to be construed as limiting the scope of the present invention. They merely illustrate some of the variations possible through the practice of this invention.

EXAMPLE 1

Fmoc-L-alanine (1.56 g, 5.0 mmoles) was suspended in 100 ml of toluene, and paraformaldehyde (1 g) and para-toluenesulfonic acid (100 mg) were added. The mixture was refluxed for 30 minutes with azeotropic water removal. The solution was cooled, washed with 1N aqueous NaHCO$_3$ (2×25 ml) and dried over Na$_2$SO$_4$. Concentration in vacuo gave 1.56 g (96%) of crystalline product, mp 142°–144°: $[\alpha]_D^{25}=72.5$ (c 1.0, CH$_2$Cl$_2$).

Anal. calcd for C$_{19}$H$_{17}$NO$_4$: C, 70.58; H, 5.30; N, 4.33, Found: C, 70.48; H, 5.38; N, 4.31.

The oxazolidinone from Fmoc-L-alanine (0.97 g, 3.0 mmoles) was dissolved in 15 ml. of CHCl$_3$ and 15 ml trifluoroacetic acid and triethylsilane (1.43 ml=1.04 g, 9.0 mmoles) was added. The solution was stirred at room temperature for 22 hrs. followed by concentration in vacuo to an oil. The oil was dissolved in CH$_2$Cl$_2$ and reconcentrated 3 times. The resultant oil crystallized on standing. The crystals were dissolved in ether and concentrated to a crystalline solid which was washed with 5% ether in hexane and dried. Yield, 0.96 g (98%), mp 154.5°–155.5°; $[\alpha]_D^{25}$ -21.4 (c 1.0, CH$_2$Cl$_2$). Mass spec. (70 eV) m/e 325 (M+).

EXAMPLE 2

Fmoc-L-alanine (1.56 g, 5.0 mmoles) was suspended in 100 ml of toluene, and cyclohexane carboxaldehyde (3.20 ml=3.45 g, 30 mmoles) and p-toluenesulfonic acid (100 mg) were added. The mixture was refluxed for 7 hrs. with azeotropic water removal. The solution was cooled, washed with 1N aqueous NaHCO$_3$ (2×25 ml) and dried over Na$_2$SO$_4$. Concentration in vacuo gave a yellow oil which was dissolved in CH$_2$Cl$_2$ and reconcentrated several times to give 3 g of amber oil. A 100 mg portion was purified by silica gel preparative tlc eluting with CHCl$_3$. The product was washed from the silica gel with CHCl$_3$ and 95:5 CHCl$_3$-MeOH to give 77 mg (77%); $[\alpha]_D^{25}$ 22.4 (c 0.5, CH$_2$Cl$_2$); Mass spec. (70 eV) m/e 405 (M+).

The oxazolidinone from Fmoc-L-alanine (20 mg, 0.045 mmole) was dissolved in 0.25 ml CHCl$_3$ and 0.25 ml trifluoroacetic acid and triethylsilane (24 μl=17.5 mg, 0.15 mmole) was added. The solution was stirred for 22.5 hrs. at room temperature followed by concentration in vacuo. Purification by silica gel chromatography gave 18 mg (91%) of amorphous product $[\alpha]_D^{25}$ -14.2 (c. 1.0, CH$_2$Cl$_2$); Mass spec., (70 eV) m/e 407 (M+).

EXAMPLE 3

A mixture of Cbz-glycine (10.46 g, 50 mmoles), paraformaldehyde (0.066 equiv.), and p-toluenesulfonic acid (500 mg) in benzene (400 ml) was refluxed for 30 min. with azeotropic water removal. The solution was cooled and washed with 1N aqueous NaHCO$_3$ (2×100 ml) and dried over Na$_2$SO$_4$. Concentration in vacuo gave a crystalline solid. Recrystallization from benzene-low boiling petroleum ether gave 5.84 g (53%) of product, mp 79°–80° (lit. mp. 84°, D. Ben-Ishai, *J. Amer. Chem. Soc.*, 79, 5736 (1957)).

The oxazolidinone from Cbz-glycine (221 mg, 1.0 mmole) was dissolved in 10 ml of CHCl$_3$ and triethylsilane (193 ||1=174 mg, 1.5 mmoles) and trifluoroacetic acid (770 μl, 10 mmoles) were added. The solution was stirred at room temperature for 2 hrs. and concentrated in vacuo. CHCl$_3$ was added and the solution was reconcentrated to a colorless oil. Silica gel chromatography gave 107 mg (48%) of Cbz-sarcosine, identified by NMR (N-Me, 2.98 ppm) and amino acid analysis.

Table 1 shows Examples 4-12 prepared in the same manner as the preceding examples; in each example, the N-protecting group is Fmoc.

TABLE 1
N—PROTECTED-OXAZOLIDINONES (II)[1]
AND
N—PROTECTED N—SUBSTITUTED α-AMINO ACIDS (III)[1]

| EXAMPLE NO. | R$^1$ | R$^2$ | Yield II | Yield III |
|---|---|---|---|---|
| 4. | —CH(CH$_3$)$_2$ | H— | 96% | 100% |
| 5. | —(CH$_2$)$_2$SCH$_3$ | H— | 87.5% | 22% |
| 6. | —CH$_2$Ph | H— | 70% | 100% |
| 7. | —(CH$_2$)$_4$ Pht[b] | H— | (a) | 70% |
| 8. | —CH$_2$O—CH$_2$Ph | H— | 98% | 96% |
| 9. | —CH$_3$ | CH$_3$— | 79% | 74% |
| 10. | —CH$_3$ | Ph— | (a) | (a) |
| 11. | —CH$_3$ | Ph—CH$_2$— | 30% | 95% |
| 12. | —CH$_2$-[imidazole]-N—DNP[b] | H— | 37% | 67% |

[a] Yield not determined
[b] Pht = phthalimidyl, DNP = dinitrophenyl
[1] The structures of Formulae II and III are:

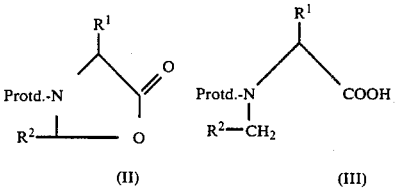

(II)    (III)

What is claimed is:

1. A process for preparing chiral, N-protected, N-substituted α-amino acids of Formula III:

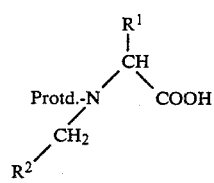

III wherein
(a) R$^1$ is loweralkyl, hydroxyloweralkyl, mercaptoloweralkyl, aminoloweralkyl, mono- or diloweralkylaminoloweralkyl, loweralkylthioloweralkyl, phenyl, benzyl, phenylloweralkyl, p-hydroxybenzyl, indolylloweralkyl, phthalimidylloweralkyl, imidazolylloweralkyl, benzyloxyloweralkyl, guanidinoloweralkyl, carboxyloweralkyl and loweralkylcarboxyloweralkyl;

(b) $R^2$ is loweralkyl, straight or branched $C_1$–$C_{22}$ alkyl, cycloloweralkyl, benzyl, phenyl, and phenylloweralkyl, carboxyloweralkyl, loweralkoxycarbonylloweralkyl and carboxyloweralkylaminoloweralkyl;

(c) Protd, is an N-protecting group selected from the group consisting of 9-fluorenylmethoxycarbonyl, trifluoroacetyl, 4-toluenesulfonylethyloxycarbonyl, carbobenzoxy, 2-chlorocarbobenzoxy, methylsulfonyl-ethyloxycarbonyl, 2-(triphenylphosphino)-ethoxycarbonyl, and 2-cyano-t-butyloxycarbonyl;

which comprises treating an N-protected oxazolidinone of Formula II:

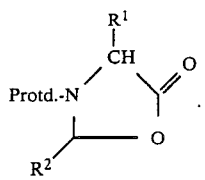

with a selective reducing agent.

2. The process of claim 1 wherein the selective reducing agent is triethylsilane/trifluoroacetic acid.

3. The process of claim 1 wherein the Protd. is fluorenylmethoxycarbonyl.

4. The process of claim 1 wherein the Protd. is carbobenzoxy.

* * * * *